United States Patent [19]

Bohandy et al.

[11] Patent Number: 4,904,929

[45] Date of Patent: Feb. 27, 1990

[54] METHOD FOR DETECTION OF WEAK LINKS IN THE CURRENT PATH OF ELECTRICALLY CONTINUOUS SUPERCONDUCTORS

[75] Inventors: Joseph Bohandy, Columbia; Boris F. Kim, Pasadena; Terry E. Phillips, Ellicott City; Frank J. Adrian, Olney; Kishin Moorjani, Silver Spring, all of Md.

[73] Assignee: The Johns Hopkins University, Baltimore, Md.

[21] Appl. No.: 325,823

[22] Filed: Mar. 20, 1989

[51] Int. Cl.⁴ .............................................. G01N 27/00
[52] U.S. Cl. ..................................... 324/71.6; 505/843
[58] Field of Search ................. 324/71.6; 505/842, 843

[56] References Cited

PUBLICATIONS

Khachatuman et al., "Changes in Microwave...", Mat. Res. Soc. Symp. Proc., vol. 99, Materials Research Society, 1988, pp. 383-386, Symposium held Dec. 4, 1987.

Kwak et al., "Evidence for Intergrannular Weak Links...", Extended Abstracts, High Temperature Superconductors II, Materials Research Society, Apr. 9, 1988, pp. 163-166.

Primary Examiner—Gerard R. Strecker
Assistant Examiner—Anthony L. Miele
Attorney, Agent, or Firm—Robert E. Archibald; Mary L. Beall

[57] ABSTRACT

Weak links in electrically continuous superconductors are detected by observing the effect of magnetic field modulation on the dc resistance of superconductors. The phase detected response to the magnetic modulation shows a peak at $T_c$. The presence of a second peak at temperatures below $T_c$, and concomitantly the appearance of a tail on the low temperature end of the dc resistance vs temperature curve indicates the presence of weak links in the superconductor.

17 Claims, 4 Drawing Sheets

TUNNELLING JUNCTION i = CURRENT
SC = SUPERCONDUCTOR
NSC = NON-SUPERCONDUCTOR

CONSTRICTION

POINT CONTACT  FIG. 1c

METHOD FOR DETECTION OF WEAK LINKS IN THE CURRENT PATH OF ELECTRICALLY CONTINUOUS SUPERCONDUCTORS

STATEMENT OF GOVERNMENTAL INTEREST

The Government has rights in this invention pursuant to Contract No. N00039-87-C-5301 awarded by the Department of the Navy.

BACKGROUND OF THE INVENTION

This invention relates to a method for detecting the existence of weak links in the current path of electrically continuous superconducting samples. The apparatus used in the method of the present invention is generally described in commonly assigned U.S. patent application Ser. No. 07/238,682 entitled "A Novel Technique for Detection of Superconductivity" filed Sept. 31, 1988 and incorporated herein by reference. The method of this invention is a variation of Ser. No. 238,682 in which the magnetically modulated electrical resistance response of the sample is phase detected and recorded as a function of temperature.

OBJECTS OF THE INVENTION

It is an object of the present invention to provide a method for the rapid and accurate detection of the presence of weak links in the current path of electrically continuous superconducting samples.

It is also an object of the present invention to determine the presence or absence of weak links by measuring the magnetically modulated electrical resistance of a sample while varying the temperature and maintaining the magnetic field below its critical value.

It is another object of the invention to provide a method to study the performance of superconductors containing weak links in response to the action of an applied magnetic field while varying the temperature.

It is also an object of the present invention to provide a method to study the behavior of superconductors containing weak links in response to changes in the magnetic field.

It is also an object of the present invention to provide a method to study the behavior of superconductors containing weak links in response to changes in applied current.

Still another object of the present invention is to provide a quality control method for the fabrication of superconducting thin films.

SUMMARY OF THE INVENTION

The present invention relates to a method to detect the presence of weak links in the current path of electrically continuous superconducting samples by measuring the magnetically modulated electrical resistance of the sample. A weak link is a connection between at least two superconducting regions which has a much lower critical current than the superconductors it connects. It can be penetrated by a magnetic field. FIG. 1 represents three examples of weak links: tunnelling junction, constriction and point contact.

The method of the invention is based on two principles:

1. At temperatures below the superconducting phase transition temperature ($T_c$), the resistance of the sample goes to zero, and 2. The superconductive phase transition temperature is magnetic field dependent.

The first principle is demonstrated graphically by FIG. 2 representing the amount of resistance in a sample in relation to temperature. The graph shows a precipitous drop in resistance at $T_c$.

According to the second principle, the application of a magnetic field at a strength below its critical value causes $T_c$ to drop to a lower value. This is graphically represented in FIG. 3 wherein an increase in magnetic field causes the $T_c$ to shift from point A to point B.

The invention combines both of these principles in a method to determine accurately and rapidly whether a particular specimen contains weak links.

According to the invention, the resistance of the sample is determined while slowly changing the temperature and also while modulating the applied magnetic field at a defined frequency. The magnetic field is maintained below its critical value which is defined as the maximum magnetic field the superconductive state can be subjected to at a temperature below $T_c$ and still remain superconductive. The critical value for the magnetic field of weak links is less than for the bulk superconductor. This allows a series of tests to be performed, each measuring the resistance of the sample at each temperature change but at different applied magnetic fields. The results can be compared and provide a method to study the behavior of weak links in superconductive samples in response to the application of different magnetic fields. The invention also provides a way to study the behavior of weak links in response to the application of different currents.

The modulation of the magnetic field must be such that the total field applied to the sample is always of the same polarity. In other words, the total field does not change direction. The temperature may be swept from high values to low values or vice versa.

The apparatus used in the method of this invention is generally described in U.S. patent application Ser. No. 07/238,682. The particular apparatus is represented in FIG. 4.

The method of the present invention is related to the method of U.S. patent application Ser. No. 07/238,682 in which the magnetically modulated electrical resistance response of the sample is phase detected and recorded as a function of temperature. It does not depend on the microwave absorption of the sample but instead uses a four-point probe technique to measure the ac or dc electrical resistance of a sample as a function of temperature and in the presence of a modulated magnetic field. Typically, the ac resistance measurement is made in the range of 10–1000 Hz.

The temperature is sequentially changed in equal increments, producing first signals at each temperature change. The resistance is determined at each temperature change, producing second signals. Each second signal is compared to the modulation frequency by phase detection, producing third signals. A series of coordinate points is plotted on an x-y recorder, wherein one axis represents the first signals and the other axis represents the third signals.

The actual result for superconducting materials not containing weak links, plotted on the x-y recorder, is proportional to the derivative of the resistance with respect to the temperature. At $T_c$ this produces a well defined peak. This relationship is demonstrated in FIG. 5 wherein 5a shows the dc resistance vs. temperature measurement for a conventional superconductor NbN and 5b shows the response obtained by the magnetically modulated electrical resistance (MAMER) method of the present invention using a 10 KHz frequency and 5 G magnetic field modulation of a 30 G dc magnetic field. The superconducting transition at approximately 15° K. is extremely sharp (see FIG. 5a) and the MAMER response (see FIG. 5b) produces a very well defined peak which is the derivative of the resistance. Note the lack of a tail on the low temperature side of the dc resistance curve and the correspondingly flat MAMER response. If the MAMER response produces a second peak at temperatures below $T_c$ concomitant with a tail on the resistance curve, this indicates the existence of weak links. Thus there are no weak links in this particular thin film.

The superconducting sample to be used in the present invention may be thin a film or bulk, either of which can be solid or granular, but must be electrically continuous.

The static magnetic field is in the range of 1 G to 5 KG. The static magnetic field modulation is in the range of 0–5 G but must be less than that of the static field. The static field is modulated at a frequency in the range of 5–100 KHz. The electric current applied to the sample is in the range of 0.1 μA-1 A.

The temperature is recorded and the resistance is determined only at equal preselected temperature increments in a linear temperature progression. The temperature range is determined experimentally and depends on the nature of the sample being tested.

BRIEF DESCRIPTION OF THE DRAWINGS

FIGS. 1a-1c are a representation of several types of weak links.

DESCRIPTION OF THE PREFERRED EMBODIMENTS

Figure 1A:
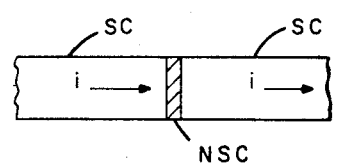
Figure 1B:
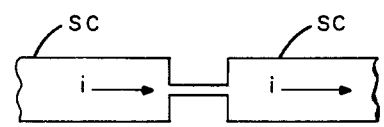
Figure 2:
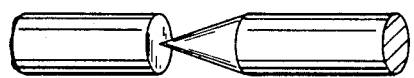
FIG. 2 is a graphic representation of the precipitous drop in resistance demonstrated by a superconductor at $T_c$.
Figure 2:
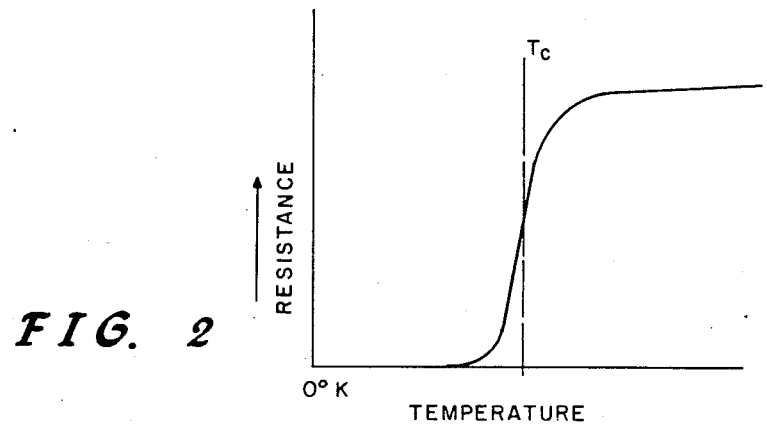
Figure 3:
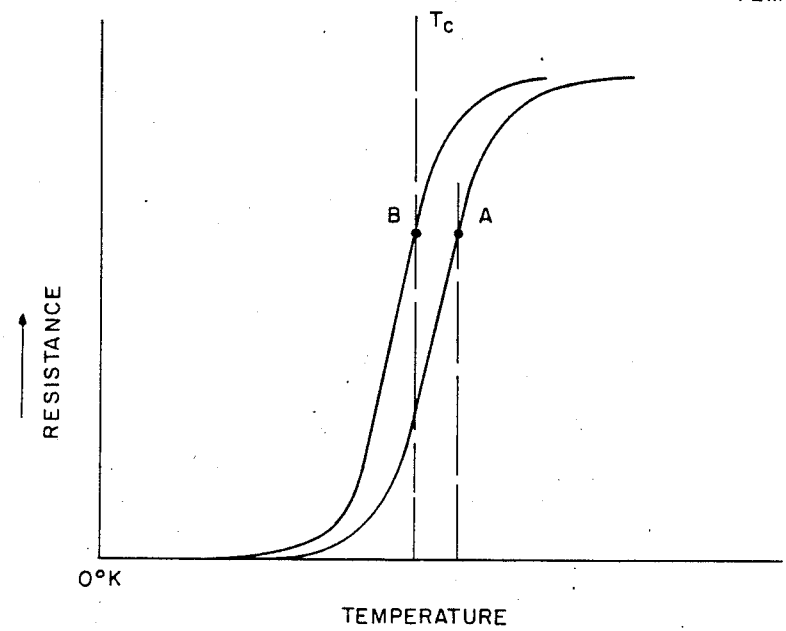
FIG. 3 is a graphic representation of the magnetic field dependence of the superconductor $T_c$.
Figure 4:
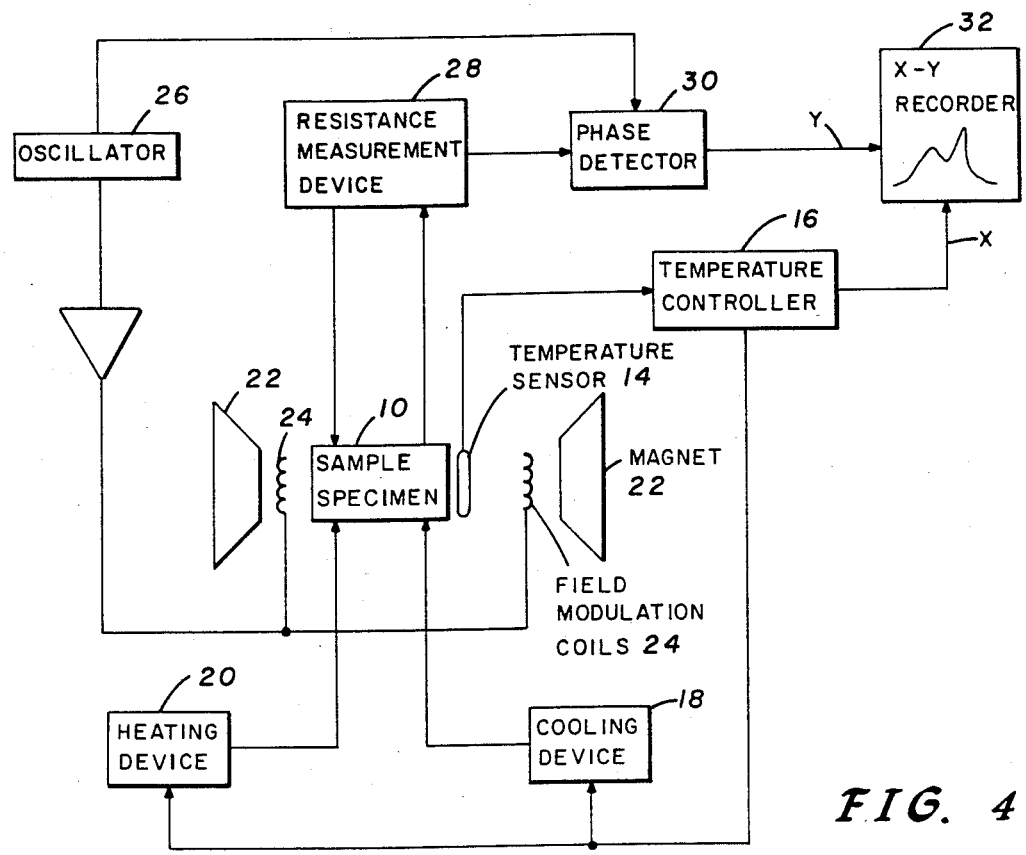
FIG. 4 is a block diagram of the apparatus used in the present invention.

The preferred embodiment shown in FIG. 4 uses a four point probe as the resistance measuring device 28 to measure the electrical resistance of an electrically continuous superconducting sample 10.

The temperature sensor 14 is connected to a temperature controller 16 controlling the temperature of the sample through the action of cooling device 18 and heating device 20.

A constant dc magnetic field of 30 G is applied to a bulk $EuBa_2Cu_3O_{7-y}$ (EBCO) superconductive sample 10 by magnet 22. This field is modulated at 5 G by the application of an ac frequency of 10 KHz supplied by oscillator 26 through field modulation coils 24. At all times the total magnetic field is of the same polarity and below the critical value for the bulk superconductor.

A 5 mA electrical current is applied to the sample via the two current leads of the four point probe and the resulting voltage is measured from the voltage leads of the probe. The voltage output from the four point probe is compared, in phase detector 30, to the signal from oscillator 26. Note that the resistance is determined according to the equation :

$$\text{Voltage} = \text{Resistance} \times \text{Current} \quad (V = RI) \tag{1}$$

As the temperature is changed or swept, changes in resistance measured by the four point probe are phase detected by phase detector 30 at the modulation frequency supplied by oscillator 26. Computer signals "y" from phase detector 30 and related computer signals "x" from temperature controller 16 form coordinate points on x-y recorder 32 as shown in FIG. 6b.

Because the resistance of the sample is magnetic field dependent and the field is modulated at 10 KHz, when the resistance is phase detected at 10 KHz, its derivative with respect to field as a function of temperature is the response actually recorded on x-y recorder 32. For superconducting materials not containing weak links, Ser. No. 07/238,682 teaches that this response is proportional to the derivative of the resistance with respect to temperature which is a peak at the transition temperature. The $T_c$ is shown as a peak at approximately 92.5° K., as demonstrated in FIG. 6b, which also shows a second weak, broad peak. When a second peak appears at temperatures below the $T_c$ and a corresponding tail appears on the d.c. resistance curve shown in FIGS. 6 and 7 and discussed below, it is due to the presence of weak links in the sample. Since weak links have a greater magnetic field dependence and a lower critical field than the bulk superconductor with no weak links, the appearance of the second MAMER peak can be optimized by operating the MAMER method at a magnetic field lower than the average weak link critical value as shown in FIGS. 6c-d. Although the critical magnetic field values are known for some superconductors with no weak links, in general, both the critical value for the superconductor with no weak links and the critical value for the weak link(s) must be determined experimentally for each sample.

In practice, the MAMER method is operated as described above. An appropriate magnetic field is imposed on the electrically continuous sample and the magnetic field is modulated in such a fashion that the total magnetic field always has the same polarity. The temperature of the sample is slowly changed and the phase detected resistance of the sample is recorded at each temperature change. The $T_c$ is identified by the appearance of a sharp peak, indicating a precipitous drop in resistance. If a second peak does appear at temperatures below $T_c$ and the corresponding dc resistance curve has a tail (FIGS. 6 and 7), the electrically continuous sample contains weak links. The appearance of the second peak can be optimized by repeating the MAMER method, at least once, at a lower magnetic field.

The method of the present invention may be operated several times on the same sample but at different magnetic fields. This provides a technique to study the behavior of weak links as a function of magnetic field or current.

DISCUSSION

FIG. 6 represents a series of MAMER spectra and their respective simultaneously recorded dc resistance curves for a bulk sample of $EuBa_2Cu_3O_{7-y}$ (EBCO) in a static magnetic field of 500 G, 30 G, 10 G and 2 G, respectively, using a 5 mA current applied to the sample. This sample was prepared by standard techniques and previously characterized by thermogravimetric analysis, x-ray powder diffraction, electrical resistance and the method of the above described application Ser. No. 238,682, indicating the presence of weak links. The MAMER response is represented in dotted lines, the dc resistance measurement is represented in solid lines and a x10 expansion of the dc resistance curve is represented in dashed lines.

Figure 5A:
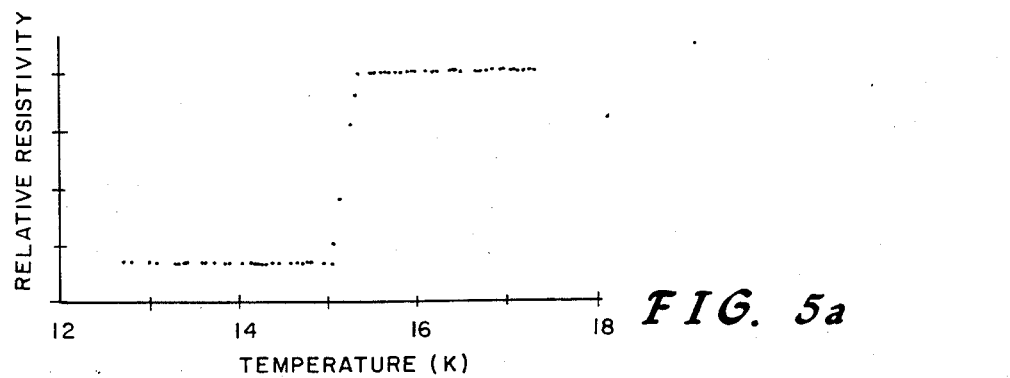
FIGS. 5a and 5b represent the dc resistance measurement and the MAMER for a conventional superconductor.
Figure 5B:
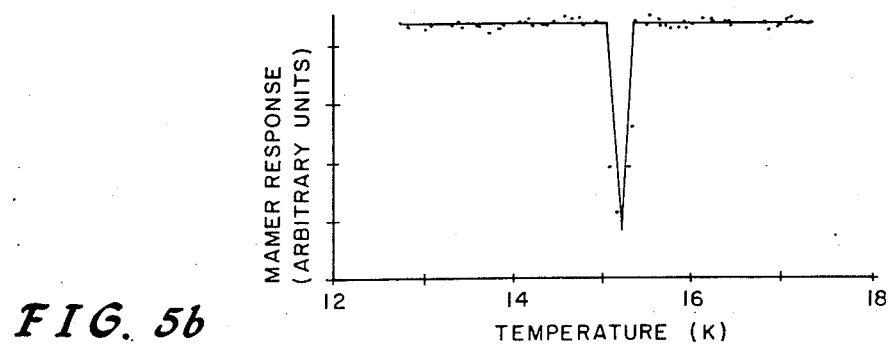
Figure 6A:
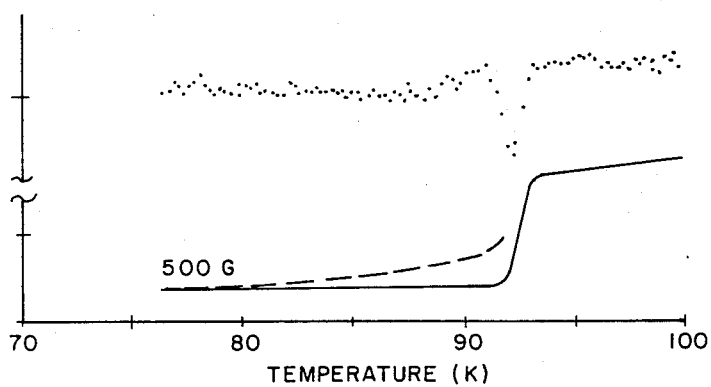
FIGS. 6a-6d show a series of MAMER spectra (dotted line), simultaneously recorded dc resistance curves (solid line) and a x10 expansion of the resistance curve (dashed line) using a current of 5 mA, a 5 G modulation amplitude for (a), (b) and (c) and a 1 G amplitude for (d) with four different static fields.
Figure 6B:
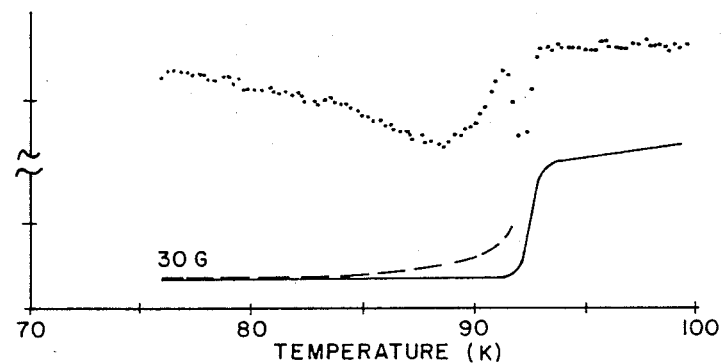
Figure 6C:
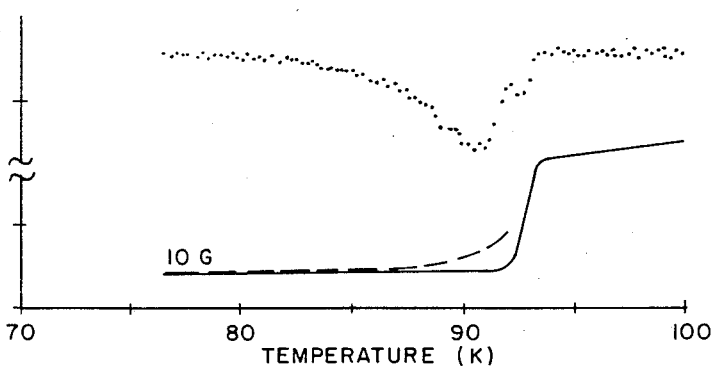
Figure 6D:
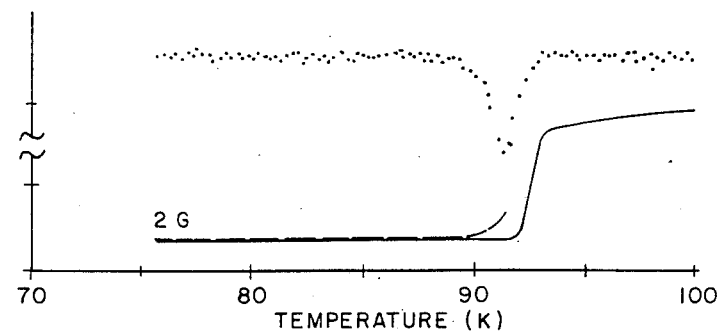

The MAMER response in a 500 G field, FIG. 6a, is characterized by a derivative peak occurring at a temperature corresponding to the inflection point in the dc resistance curve. Qualitatively, this behavior is similar to that exhibited by the NbN film in FIG. 5b. An additional, though more subtle, feature is also observed on the low temperature side of the main transition, where there is a weak, very broad peak in the MAMER response. Note also in the x10 expansion of the resistance curve that there is a corresponding significant tail on the low temperature side of the primary resistance transition.

As the static field is reduced to 30 G, FIG. 6b, the resistance tail has been reduced considerably; clearly the extent of this resistive tail is dependent on the magnitude of the applied magnetic field. Correspondingly the weak peak on the low temperature side of the primary MAMER peak has evolved into a broad, reasonably well-defined peak, which results from the magnetic field dependence of the weak links.

Lowering the static field to 10 G, FIG. 6c, results in a continued reduction of the resistive tail, and concomitantly a narrowing and shift to higher temperature of the secondary MAMER peak, effecting an increased amplitude relative to the primary peak. In a 2 G static field and with a 1 G modulation amplitude, FIG. 6d, the tailing is further reduced and the primary peak is barely discernible as a weak shoulder on the secondary peak. Note that there is a lower magnetic field limit here because the sensitivity is proportional to the field modulation amplitude, and because a dc bias field greater than the modulation field is required. The response of the weak links now dominates.

As shown above, the high sensitivity of the MAMER response to weak links and the manifestation of weak link superconductivity as a secondary peak below the bulk $T_c$ are both a result of the much larger magnetic field dependence of weak link resistance compared to that of the bulk superconductor.

Figure 7A:
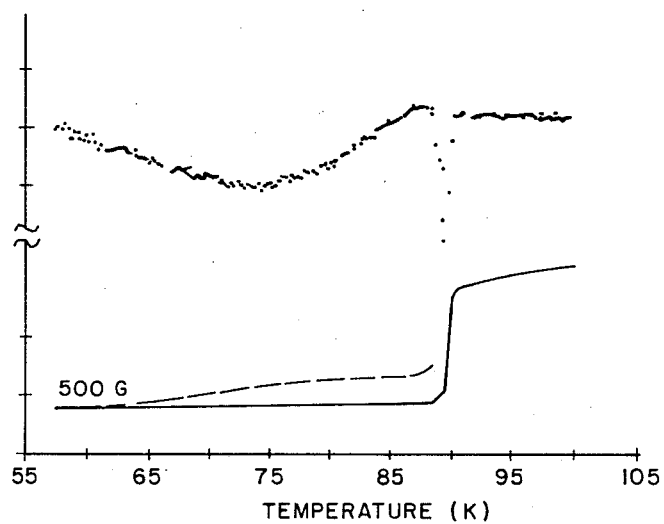
FIGS. 7a and 7b show MAMER spectra (dotted line), simultaneously recorded dc resistance curves (solid line) and a x10 expansion of the resistance curve (dashed line) using a 100mA current, a 5 G modulation amplitude and two different static magnetic fields.
Figure 7B:
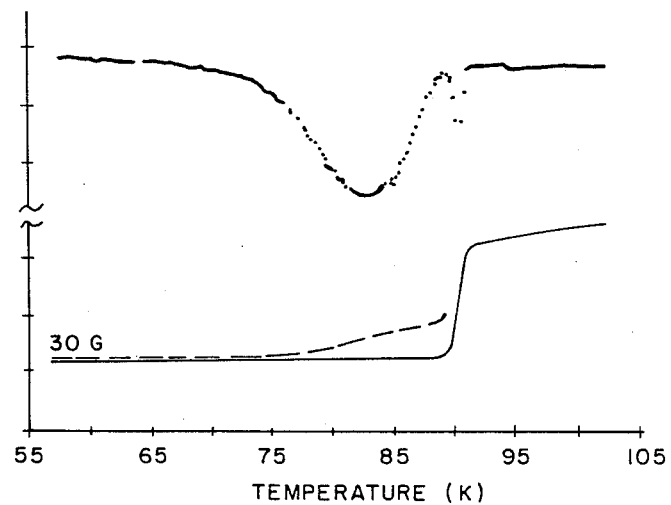

Note that FIG. 7 shows the MAMER response with a 100 mA current in a 30 G and 500 G dc magnetic field. An examination of FIGS. 6b and 7b shows a shift in the sharp peak, as well as in the second peak, when the current is increased from 5 mA to 100 mA in a 30 G magnetic field. The shift is also observed when comparing FIGS. 6a and 7a. Thus, the MAMER method can also be used to study the behavior of weak links in response to the application of different currents imposed on the sample.

The presence of a tail on the low temperature side of the resistance curve is difficult to determine as shown in FIGS. 6 and 7 unless the tail has been multiplied by 10 (see the dash lines). However, the corresponding MAMER response is a relatively strong second peak on the x - y recorder, indicating the presence of weak links. By changing the static magnetic field or the imposed current, the behavior of the weak links in response to varying conditions may be studied.

The MAMER method has also been used to test for weak links in $YBa_2Cu_3O_{7-y}$ and BiSrCaCuO with similar results.

Computer means, not shown, facilitate the operation of the process of the invention. Typical software used in the computer means is disclosed in Ser. No. 07/238,682, incorporated by reference.

The invention described is not intended to be limited to the embodiments disclosed but includes modifications made within the true spirit and scope of the invention.

What is claimed is:

1. A method for detecting weak links in a current path of an electrically continuous superconducting sample comprising:
    (a) providing the electrically continuous superconducting sample;
    (b) imposing a magnetic field on the sample;
    (c) modulating the imposed magnetic field in such a fashion that the total magnetic field is always of the same polarity;
    (d) sequentially changing the temperature of the sample, recording the temperature at each change and producing first signals;
    (e) determining the resistance of the sample at each temperature change and producing second signals;
    (f) comparing the second signals to the modulation frequency by phase detection and producing third signals;
    (g) plotting a series of coordinate points where one axis represents said first signals and the other axis represents said third signals; and
    (h) measuring the dc resistance of the sample as a function of temperature to obtain a dc resistance curve;

wherein the $T_c$ of the superconducting sample is indicated by the presence of a first peak formed by the series of coordinate points and a corresponding precipitous drop in resistance on the resistance curve and further wherein the existence of weak links in the superconducting sample is indicated by the presence of a second peak formed by the series of coordinate points at a lower temperature than the first peak and a corresponding tail on the low temperature end of the resistance curve.

2. A method according to claim 1, wherein the temperature is recorded and the resistance is measured only at equal preselected temperature increments in a linear temperature progression.

3. A method according to claim 1, wherein the resistance of the sample is measured using one of a two point probe and a four point probe.

4. A method according to claim 1, wherein said first signal is the temperature and said third signal is the phase detected resistance with respect to the temperature.

5. A method according to claim 1, wherein the $T_c$ is identified by the location of the peak in reference to said one axis representing said first signals.

6. A method according to claim 1, wherein the sample is one of a thin film superconductor, a bulk solid superconductor and a bulk granular superconductor.

7. A method according to claim 1, wherein the resistance in step e is determined by:
   (i) applying a current to the sample,
   (j) measuring the resulting voltage and,
   (k) calculating the resistance according to the equation V=RI.

8. A method according to claim 3, wherein the resistance is determined using the four point probe and further wherein an electrical current is applied to the sample via two current leads of the four-point probe, the resulting voltage is measured from the voltage leads of the probe and the resistance is calculated according to the formula V=RI.

9. A method according to claim 1, including repeating steps a–h at least one time, each repeat of step b using a different magnetic field with each different magnetic field being lower than that used previously.

10. A method according to claim 7, including repeating steps a–h at least one time, each repeat of step e using a different applied current with each different applied current being lower than that used previously.

11. A method according to claim 1, wherein steps g and h occur simultaneously.

12. A method for detecting weak links in a current path of an electrically continuous superconducting sample comprising:
   (a) providing the electrically continuous superconducting sample;
   (b) imposing a magnetic field in the range of 1G to 5KG on the sample;
   (c) modulating the imposed magnetic field, in the range >0–5G and at a frequency in the range of 5–100 KHz, in such a fashion that the total magnetic field is always of the same polarity;
   (d) sequentially changing the temperature of the sample, recording the temperature at each change and producing first signals;
   (e) applying a current in the range of 0.1 $\mu A$–1 A to the sample, measuring the resulting voltage at each temperature change and producing second signals;
   (f) comparing the second signals to the modulation frequency by phase detection and producing third signals;
   (g) plotting a series of coordinate points where one axis represents said first signals and the other axis represents said third signals; and
   (h) measuring the dc resistance of the sample as a function of the temperature to obtain a dc resistance curve;
wherein the $T_c$ of the superconducting sample is indicated by the presence of a first peak formed by the series of coordinate points and a corresponding precipitous drop in resistance on the resistance curve and further wherein the existence of weak links in the superconducting sample is indicated by the presence of a second peak formed by the series of coordinate points at a lower temperature than the first peak and a corresponding tail on the low temperature end of the resistance curve.

13. A method according to claim 12, wherein the sample is one of a thin film superconductor, a bulk solid superconductor and a bulk granular superconductor.

14. A method according to claim 12, including repeating steps a–h at least one time, each repeat of step b using a different magnetic field with each different magnetic field being lower than that used previously.

15. A method according to claim 12, including repeating steps a–h at least one time, each repeat of step e using a different applied current with each different applied current being lower than that used previously.

16. A method according to claim 12, wherein steps g and h occur simultaneously.

17. A method for detecting weak links in a current path of an electrically continuous superconducting sample comprising:
   providing the electrically continuous superconducting sample;
   imposing a magnetic field of 30 G on the sample;
   modulating the imposed magnetic field at 5 G and at a frequency of 10 KHz, in such a fashion that the total magnetic field is always of the same polarity;
   sequentially changing the temperature of the sample, recording the temperature at each change and producing first signals;
   applying a current of 5 ma to the sample, measuring the resulting voltage at each temperature change and producing second signals;
   comparing the second signals to the modulation frequency by phase detection and producing third signals;
   plotting a series of coordinate points where one axis represents said first signals and the other axis represents said third signals; and
   measuring the dc resistance of the sample as a function of the temperature to obtain a dc resistance curve;
wherein the $T_c$ of the superconducting sample is indicated by the presence of a first peak formed by the series of coordinate points and a corresponding precipitous drop in resistance on the resistance curve and further wherein the existence of weak links in the superconducting sample is indicated by the presence of a second peak formed by the series of coordinate points at a lower temperature than the first peak and a corresponding tail on the low temperature end of the resistance curve.

* * * * *